United States Patent [19]

Kovacs et al.

[11] 4,299,972
[45] Nov. 10, 1981

[54] PREPARATION OF CYCLOPROPANECARBOXYLIC ACID ESTERS

[75] Inventors: Gabor Kovacs, Budapest; Istvan Szekely, Dunakeszi; Marianne Lovasz nee Gaspar, Budapest; Rudolf Soos, Budapest; Joszef Dukai, Budapest, all of Hungary

[73] Assignee: Chinoin Gyógyszer és Vegyészeti Termekék Gyara Rt., Budapest, Hungary

[21] Appl. No.: 164,902

[22] Filed: Jul. 1, 1980

[30] Foreign Application Priority Data

Jul. 2, 1979 [HU] Hungary ................................ CI 1945

[51] Int. Cl.³ .............................................. C07C 67/18
[52] U.S. Cl. ............................ 560/124; 260/326 NS; 260/343.3 P; 260/465 D; 260/501.15
[58] Field of Search ................... 560/124; 260/465 D, 260/326 A, 343.3 P, 326 NS

[56] References Cited

U.S. PATENT DOCUMENTS 3,832,375  8/1974  Itoh ...................................... 560/124
4,024,163  5/1977  Elliott .................................. 560/124
4,248,888  2/1981  Szekely ............................... 424/306

FOREIGN PATENT DOCUMENTS 874394  6/1979  Belgium.

OTHER PUBLICATIONS

Szekely, Tetrahedron Letters, No. 49, pp. 4505–4506, (1976).

Primary Examiner—Natalie Trousof
Assistant Examiner—Michael Shippen
Attorney, Agent, or Firm—Karl F. Ross

[57] ABSTRACT

A process is disclosed for the preparation of an optically active or racemic cyclopropanecarboxylic acid of the formula (I)

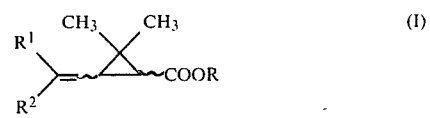

wherein
$R^1$ and $R^2$ are the same or different and each is lower alkyl or halogen;
R is a member of a group which contains various cyclic structures as set forth in the specification,
the ∼ valency bond represents α- and/or β-configuration;
the — valency bond represents β-configuration,
which comprises reacting an optically active or racemic cyclopropanecarboxylic acid of the formula (VII)

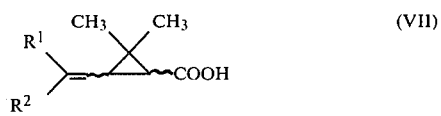

with a dimethyl-methylidene-ammonium salt of the formula (VIII)

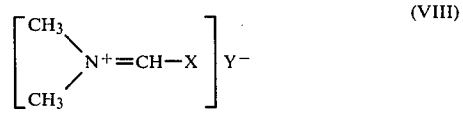

wherein
X is halogen or lower alkoxy and
$Y^-$ is a halide or lower alkylsulfate ion in an anhydrous, inert organic solvent, and sebsequently reacting a dimethyl-acloxy-methylidene-ammonium salt thus obtained with an optically active, inactive or racemic alcohol of the formula

R—OH without isolation, in the presence of an organic base.

12 Claims, No Drawings

PREPARATION OF CYCLOPROPANECARBOXYLIC ACID ESTERS

This invention relates to a process for the preparation of cyclopropanecarboxylic acid esters.

More particularly the invention is concerned with the preparation of optically active or racemic cyclopropanecarboxylic acid derivatives of the formula (I)

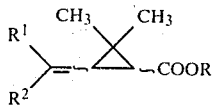

wherein
$R^1$ and $R^2$ are the same or different and represent lower alkyl or halogen;
R represents a group of the formula (II), (IV) or (VI)

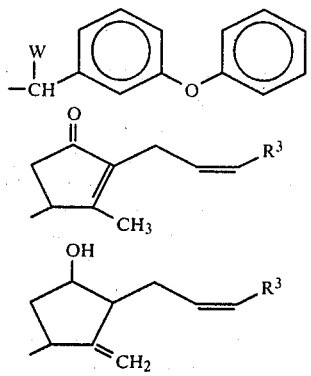

wherein
W is hydrogen, cyano or ethynyl; and
$R^3$ is straight or branched chain lower alkyl or 1-alkenyl or hydrogen; or
R is a group of the formula (III) or (V)

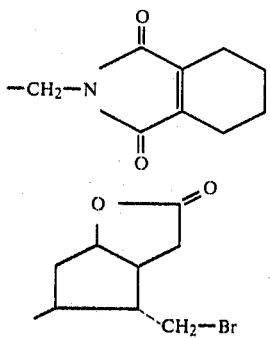

or a benzyl group.
the ~ valency bond represents α- and/or β-configuration;
the — valency bond represents β-configuration.

In the new process of the present invention the said optically active or racemic compounds of the formula (I) are prepared by reacting an optically active or racemic cyclopropanecarboxylic acid of the formula (VII)

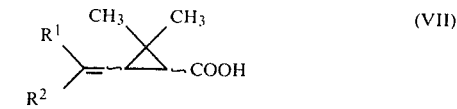

wherein $R^1$, $R^2$, ~ and — are as defined above, with a dimethyl-methylydene-ammonium salt of the formula (VIII)

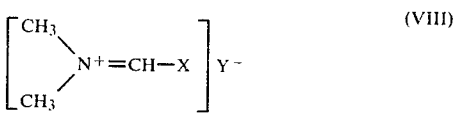

wherein
X is halogen or a lower alkoxy and
$Y^-$ is a halide or lower alkylsulfate ion—in an anhydrous, inert organic solvent, and subsequently reacting the dimethyl-acyloxy-methylydene-ammonium salt thus obtained, with an optionally optically active of racemic alcohol or the formula

R—OH wherein R is as defined above, without isolation, in the presence of an organic base.

The term "lower alkyl" means straight or branched chained alkyl groups having 1 to 4 carbon atoms (e.g. methyl, ethyl, n-propyl, isopropyl, n-butyl, etc.). The term "1-alkenyl" covers straight or branched chained lower alkenyl groups having 2 to 5 carbon atoms (e.g. vinyl, prop-1-enyl, etc.). The term "alkoxy" is used herein to refer to an alkoxy group having 1 to 4 carbon atoms (e.g. methoxy, ethoxy, etc.). The term "lower alkylsulfate" refers to alkylsulfate groups having 1 to 4 carbon atoms in the alkyl moiety (e.g. methylsulfate, ethylsulfate, etc.). The term "halogen" encompasses fluorine, chlorine, bromine and iodine atoms.

The cyclopropanecarboxylic acid esters of the formula (I) belong to the well known insecticides, called pyrethroids and pyrethrins, or if R represents a group of the formula (V) or of the general formula (VI) to compounds useful as intermediates in the synthesis of pyrethrins.

For example compounds of the formula (I), in which R is a group of the formula (V) can be reduced by complex metal hydrides to the corresponding lactols. Wittig-alkylation of the lactols obtained provided compounds of the formula (I), in which R represents the groups of the formula (VI). By oxidative rearrangement of the latter compounds cyclopropanecarboxylic acid esters of the formula (I), in which R is a group of the formula (IV) are obtained. Due to their great practical importance numerous methods have been developed for the preparation of these and similar compounds [M. Elliott: Synthetic Pyretroids, ACS Symposium series 42, 1977; Casida, Pyrethrum, Academic Press, 1973].

An ester synthesis in which a cyclopropanecarboxylic acid of the formula (VII) prepared separately would directly be reacted with an alcohol of the formula R—OH would have high technological advantages. A similar synthesis is disclosed in the Hungarian patent specification No. 170,866. According to this process the suitable acid or alcohol component is converted into an activated derivative in a previous reaction step. Suitable activated derivatives are for example acid chlorides or esters of the alcohol component with hydrochloric acid. The esterification is then carried out using these activated derivatives. The previous preparation of activated derivatives obviously increases the losses of the ester synthesis, accordingly the yield calculated either for the acid or for the alcohol component is decreased. An additional disadvantage of the synthesis is that due to the sensitive acid or alcohol component only mild reaction conditions can be employed.

It is well known [Helv., 42, 1653 (1959)] that the reaction of dimethyl formamide with phosphorus pentachloride, phosphorus oxychloride, phosphorus trichloride, thionyl chloride, phosgene and oxalyl chloride provides dimethyl-chloromethylene-ammonium chloride. It is also known [Angew. Chem. 73, 493 (1961); Chem. Ber., 96, (1963)] that by reacting anhydrous dimethyl formamide with dimethyl sulfate or diethyl sulfate dimethyl-methoxymethylydene-ammonium methylsulfate or dimethyl-ethoxymethylydene-ammonium methylsulfate is formed, which has an analogous structure. The reaction of these substituted dimethyl-methylydene-ammonium salts with carboxylic acids yield dimethyl-acyloxy-methylydene-ammonium salts. The acyloxy derivatives obtained react with amines to give acid amines in a manner known in the art [Tetr. Lett. 4, 9 to 12 (1960)]. A laboratory esterification process by means of acyloxy derivatives for the preparation of complicated esters is disclosed in Helv., 61, 1675–1681 (1978).

Our intention was to develop a new process, which is devoid of the disadvantages of the above described known processes and is suitable for the preparation of cyclopropanecarboxylic acid esters of the formula (I) even on an industrial scale, with an excellent yield.

It has surprisingly been found that an excellent synthesis method is obtained for the preparation of cyclopropanecarboxylic acid esters of the formula (I) if acids of the general formula (VII) are reacted with dimethyl-methylydene-ammonium salts of the formula (VIII) in the presence of an anhydrous, inert, organic solvent, and the dimethyl-acyloxy-methylydene-ammonium salt obtained is further reacted with alcohols of the formula ROH. In the above formulae R, $R^1$, $R^2$, X and $Y^-$ have the same meanings as hereinbefore defined.

The dimethyl-methylydene-ammonium salts of the formula (VIII) used as starting compounds can conveniently be prepared from dimethyl formamide and di-(lower)-alkyl sulfates or halogenating agents in an inert, anhydrous organic solvent. Suitable dialkyl sulfates are for example dimethyl sulfate and diethyl sulfate, and typical representative of the suitable halogenating agents are oxalyl chloride, phosgene, phosphorus trichloride, phosphorus pentachloride, phosphorus oxychloride and thionyl chloride. The use of halogenating agents from which gaseous by-products are formed during reaction is preferred. Such halogenating agents include oxalyl chloride, phosgene and thionyl chloride. In this case the reaction is completed in several minutes and dimethyl-chloromethylydene-ammonium chloride precipitates from the reaction mixture as a pure, crystalline product. The reaction is preferably carried out between −20° C. and 0° C. The reactant obtained need not be isolated, the acid of the formula (VI) can directly be added to the reaction mixture after the completion of the first reaction step.

Dimethyl-chloromethylydene-ammonium chloride reacts with the acid of the formula (VII) very rapidly to provide dimethyl-acyloxy-methylydene-ammonium chloride, which generally is homogeneously dissolved in the solvent used for the preparation of the reactant. This reaction step is performed at a temperature between −20° C. and 0° C.

The dimethyl-acyloxy-methylydene-ammonium salt prepared as described above is reacted with the alcohol component of the formula R—OH to be acylated without isolation. The reaction can be accomplished between −20° C. and room temperature, but preferably is carried out between 0° C. and room temperature. Acylation is carried out by admixing the reaction mixture containing the dimethyl-acyloxy-methylydene-ammonium salt with a mixture of the alcohol component to be acylated and an organic base, preferably an organic tertiary amine. For 1 mole of the dimethyl-acyloxy-methylydene-ammonium salt at least 1 mole of an organic base should be employed but slight excess of the organic base is preferred. The alcohol component to be acylated and dimethyl-acyloxy-methylydene-ammonium salt can principally be used in equimolar amounts, but a slight excess of the more readily accessible reactant favors the progress of the reaction. In the given temperature range acylation takes place in several minutes and esters of the formula (I) can be isolated from the reaction mixture.

As the anhydrous, inert, organic solvent numerous organic solvents are employed. Thus for example aliphatic or aromatic, optionally halo-substituted hydrocarbons, ethers, nitriles or optional mixtures thereof can be used. Preferred solvents are acetonitrile and toluene. As organic bases preferably tertiary amines, more preferably pyridine and triethyl amine are used.

Cyclopropanecarboxylic acid esters of the formula (I) can be isolated from the reaction mixture obtained after esterification by methods known per se. The reaction mixture is preferably diluted with a water-immiscible organic solvent, the solution is washed and the solvent is eliminated from the organic phase. The evaporation residue if desired, can further be purified, for example by chromatography.

By the process according to the invention cyclopropanecarboxylic acid esters of the formula (I) can be prepared by quick reactions, which are devoid of undesired side-reactions, in one reaction pot. The synthesis can easily be accomplished also on industrial scale.

Further details of the present invention are to be found in the Examples which serve merely for illustration and not limitation.

EXAMPLE 1

Preparation of 3-methyl-2-(but-2-cis-enyl)-1-oxocyclopent-2-en-4β-yl-(+)-trans-chrysanthemate (Cinerin I)

A mixture of 6 ml. of dry dimethyl formamide and 3 ml. of dry acetonitrile is cooled to −20° C. with a mixture of carbon tetrachloride and dry ice. To the cooled mixture a solution of 0.63 g. (5 mmoles) of oxalyl chloride in 2 ml. of dry acetonitrile is added. Gas evolution and the precipitation of a yellow solid can be observed. The reaction mixture is stirred at −15° C. for 15 minutes, a solution of 0.84 g. (5 mmoles) of (+)-trans-chrysanthemic acid in 2 ml. of dry acetonitrile is added and stirring is continued for further 30 minutes at 0° C. The reaction mixture is then cooled to −20° C. and 3 ml. of dry pyridine are added followed by the addition of a solution of 0.49 g. (3 mmoles) of (+)-cinerolon in 2 ml. of dry acetonitrile. Thereafter the mixture is stirred at 15° to 20° C. for 2.5 hours. The progress of the reaction is monitored by thin layer chromatography, with a 4:1 mixture of petroleum ether and ethyl acetate as a developing solvent.

The reaction mixture is taken up in 40 ml. of ether, washed with 50 ml. of water and the aqueous phase is extracted with two 40-ml. portions of ether. The organic phases are combined, dried over anhydrous magnesium sulfate and evaporated under reduced pressure, at 40° C. 1.2 g. of cinerin I are obtained.

The crude product is purified using a silica gel column of 100 g. and by elution with a 15:1 mixture of petroleum ether and ethyl acetate.

The fractions corresponding to $R_f=0.62$ (a 4:1 mixture of petroleum ether and ethyl acetate) in thin layer chromatography are collected and evaporated under reduced pressure, at 25° to 30° C. 0.663 g. (2.1 mmoles) of the title compound are obtained. Yield: 70%. $R_f=0.62$ (a 4:1 mixture of petroleum ether and ethyl acetate)

IR spectrum (film): $\nu_{max}=2900, 1715, 1660, 1180, 1140$ and $840$ cm$^{-1}$.

NMR spectrum (CDCl$_3$) $\delta=5.7$ (m, 1 H, C$\underline{H}$-O-C); 5.2–5.6 (m, 2 H, cis-olefine); 4.95 (m, 1 H =C$\underline{H}$); 2.04 (s, 3 H, =C—CH$_3$); 1.14, 1.27 and 1.73 (s+s+s, 3 H+3 H+6 H 4 methyl); 1.72 (d, 3 H, =CH—CH$_3$) ppm.

Specific rotatory power: $[\alpha]_D^{25}=-27°$ (c=2, hexane).

EXAMPLE 2

Preparation of 1-phenoxybenzyl-[3-(2,2-dichlorovinyl)-2,2-dimethyl-cyclopropanecarboxylate] (permetrin)

A mixture of 12 ml. of dry dimethyl formamide and 6 ml. of dry acetonitrile is cooled to −20° C. with a mixture of carbon tetrachloride and dry ice. To the cooled mixture a solution of 1.26 g. (0.01 moles) of oxalyl chloride in 5 ml. of dry acetonitrile is added. Gas evolution and the precipitation of a yellow solid can be observed. The reaction mixture is stirred at −15° C. for 15 minutes, whereupon a solution of 2.09 g. (0.01 moles) of 3-(2,2-dichlorovinyl)-2,2-dimethyl-cyclopropanecarboxylic acid in 5 ml. of dry acetonitrile is added. A clear solution is obtained. The reaction mixture is stirred at 0° C. for 30 minutes, cooled to −20° C. and a solution of 1.33 g. (0.006 moles) of m-phenoxy-benzylalcohol in 6 ml. of dry pyridine is added. When the addition is completed the reaction mixture is stirred at 15° to 20° C. for 2 to 2.5 hours. The progress of the reaction is monitored by thin layer chromatography.

The reaction mixture obtained when the reaction is completed can be manufactured by the following processes.

(a) The reaction mixture is taken up in 150 ml. of dichloromethane and the solution is shaken with 30 ml. of water. The organic phase is washed with five 40-ml. portions of a 5% aqueous sodium carbonate solution, and subsequently by 40 ml. of water. The aqueous phases are combined, and the dichloromethane phase is dried with anhydrous magnesium sulfate and evaporated under reduced pressure. As an evaporation residue 2.12 g. (90.5% calculated for the alcohol component) of the title compound are obtained.

The combined aqueous phases are adjusted to pH 1 with a 5 N aqueous hydrochloric acid solution and shaken with three 50-ml. portions of dichloromethane. The dichloromethane phases are combined, dried over anhydrous magnesium sulfate and evaporated under reduced pressure. As a residue 0.62 g. of 3-(2,2-dichlorovinyl)-2,2-dimethyl-cyclopropanecarboxylic acid are obtained (75% of the excess acid). Subtracting the regenerated acid from the starting amount of acid, the yield related to the acid is 77.1%.

(b) The reaction mixture is taken up in 50 ml. of dichloroethane and the solution is shaken with two 50-ml. portions of water. The organic phases are combined, dried over anhydrous magnesium sulfate and evaporated. 3 g. of the named compound are obtained.

The obtained crude product is purified by chromatography on a column filled with 100 g. of silica gel using a 5:01 mixture of petroleum ether and ethyl acetate for elution. The fractions corresponding to $R_f=0.40$ and $R_f=0.48$ (a 15:1 mixture of petroleum ether and ethyl acetate) in thin layer chromatography are collected and evaporated under reduced pressure. 1.92 g. (81.7% calculated for the alcohol component) of the pure compound are obtained.

$R_f=0.40$ and 0.48 (a 15:1 mixture of petroleum ether and ethyl acetate)

$R_f=0.61$ and 0.69 (benzene)

IR spectrum (film): $\nu_{max}=3100-2875, 1728, 1590$ and $1493$ cm$^{-1}$.

NMR spectrum (CDCl$_3$): $\delta=7.5-6.9$ (m, 9H, aromatic protons); 6.25 and 5.6 (d, 1H, trans and cis =C$\underline{H}$-); 5.1 and 5.05 (s, 2H, trans, cis-molecule, —CH$_2$-C$_6$H$_5$); 1.25 and 1.15 (s, 6H, —CH$_3$).

The product compound is obtained as a cis, trans isomeric mixture (the starting cyclopropanecarboxylic acid was also as isomeric mixture) and accordingly, the spectrum of the product includes bands corresponding to both isomers. The proton intensities indicated relate to the sum of the two isomers.

EXAMPLE 3

Preparation of 3-phenoxybenzyl-[3-2,2-dichlorovinyl)-2,2-dimethyl-cyclopropanecarboxylate] (permetrin)

Following the procedure described in Example 2 but using a solution of 0.98 g. (0.01 moles) of phosgene in 1 ml. of toluene instead of oxalyl chloride the product compound is obtained. Yield: 1.99 g. (85%). The physical and chemical characteristics of the product are identical with those given in Example 2.

EXAMPLE 4

Preparation of benzyl-[3-(2,2-dimethylvinyl)-2,2-dimethyl-cyclopropanecarboxylate]

Following the procedure described in Example 2 but replacing 3-(2,2-dichlorovinyl)-2,2-dimethyl-cyclopropanecarboxylic acid by 1.68 g. (0.01 moles) of chrysanthemic acid and m-phenoxy-benzylalcohol by 0.64 g. (0.006 moles) of benzyl alcohol, the product compound is obtained. Yield: 1.41 g. (91%).

$R_f=0.60$ (benzene).

NMR spectrum (CDCl$_3$): $\delta$ 7.5–7.2 (m, 5H, aromatic protons); 5.35 (m, cis =CH-); 5.1 and 5.05 (s, 1H, —C$\underline{H}$-2—C$_6$H$_5$); 4.9 (M, 1H, trans =C$\underline{H}$-); 1.14, 1.2 and 1.7 (s+s+s; 3H+3H+6H).

EXAMPLE 5

Preparation of 3-phenoxybenzyl-[3-(2,2-dimethylvinyl)-2,2-dimethyl-cyclopropanecarboxylate]

Following the procedure described in Example 2 but using 1.68 g. (0.01 moles) of chrysanthemic acid instead of 3-(2,2-dichlorovinyl)-2,2-dimethyl-cyclopropane carboxylic acid, the product compound is obtained.

Yield: 1.93 g. (92%).

$R_f = 0.45$ (benzene).

NMR spectrum (CDCl$_3$): δ=7.4–6.8 (m, 9H, aromatic protons); 5.35 (m, cis =C$\underline{H}$—); 5.1 and 5.05 (s, 1H, =C$\underline{H}$—); 1.14, 1.25 and 1.7 (s+s+s, 3H+3H+6H).

EXAMPLE 6

Preparation of 1β-hydroxy-2β-(cis-but-2-enyl)-3-methylene-cyclopent-4β-yl(+)-transchrysanthemate Following the procedure described in Example 1 but using 0.50 g. (3 mmoles) of 4β-hydroxy-3-methylene-2β-(cis-but-2-enyl)-1β-cyclopentanol instead of (+)-cinerolon the product compound is obtained.

Yield: 0.68 g. (72.1%).

$R_f = 0.48$ (4:1 mixture of petroleum ether and ethyl acetate).

IR spectrum (film) $\nu_{max} = 3500$, 2940, 1725, 1430, 1380, 1180, 1150, 1110 and 850 cm$^{-1}$.

NMR spectrum (CDCl$_3$) δ=5.7 (m, 1H, CH-OC); 5.4–5.7 (m, 2H, cis-olefine); 5.2–5.34 (m, 2H, =C$\underline{H}_2$); 4.2 (m, 1H, C$\underline{H}$—OH); 1.42; 1.7, 1.2 (s+s+s, 3H+3H+6H, 4 methyl); 1.72 (d, 3H, =C—C$\underline{H}_3$).

We claim:

1. A process for the preparation of an optically active or racemic cyclopropanecarboxylic acid derivative of the formula (I)

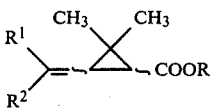

wherein

R$^1$ and R$^2$ are the same or different and each is lower alkyl or halogen;

R is selected from the group consisting essentially of the formula (II), (IV) or (VI)

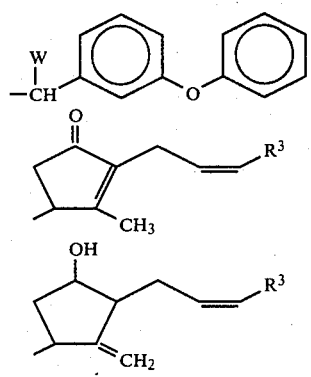

wherein

W is hydrogen, cyano or ethynyl; and

R$^3$ is a straight or branched chain lower alkyl or 1-alkenyl or hydrogen; or

R is a group of the formula (III) or (V)

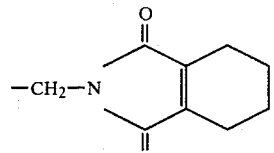

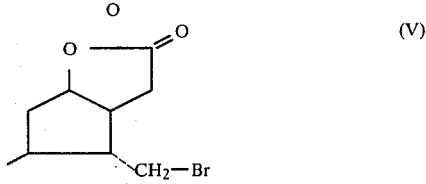

or a benzyl group, the ~ valency bond represents α- and/or β-configuration;

the — valency bond represents β-configuration, which comprises reacting an optically active or racemic cyclopropanecarboxylic acid of the formula (VII)

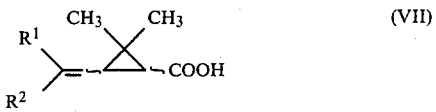

with a dimethyl-methylidene-ammonium salt of the formula (VIII)

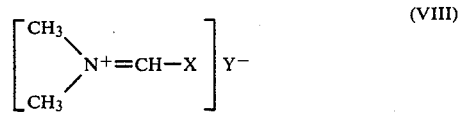

wherein

X is halogen or lower alkoxy and

Y$^-$ is a halide or lower alkylsulfate ion in an anhydrous, inert organic solvent, and subsequently reacting a dimethyl-acyloxy-methylydene-ammonium salt thus obtained with an optically active, inactive or racemic alcohol of the formula

R—OH without isolation, in the presence of an organic base.

2. A process according to claim 1 wherein acetonitrile is employed as said anhydrous, inert organic solvent.

3. A process according to claim 1 wherein a mixture of acetonitrile or toluene is employed as said anhydrous, inert organic solvent.

4. A process according to claim 1, claim 2 or claim 3 wherein a tertiary amine is employed as an organic base.

5. A process according to claim 4 wherein pyridine or triethyl amine is employed as said tertiary amine.

6. A process according to claim 1 wherein an optically active or racemic cyclopropanecarboxylic acid of the formula (VII) is reacted with a dimethyl-methylydene-ammonium salt of the formula (VIII) at a temperature between −20° C. and 0° C.

7. A process according to claim 1 wherein the dimethyl-acyloxy-methylydene-ammonium salt obtained is reacted with an optionally optically active or racemic alcohol of the formula R—OH at a temperature between −20° C. and 25° C.

8. A process according to claim 1 for the preparation of 2-methyl-3-(cis-but-2-enyl)-4-oxo-cyclopent-2-en-1-yl-(+)-trans-chrysanthemate which comprises reacting (+)-trans-chrysanthemic acid with dimethyl-chloromethylydene-ammonium chloride and further reacting the dimethyl-(+)-trans-chrysanthemoyloxy-methylydene-ammonium chloride obtained with (+)-cinerolone in the presence of said organic base.

9. A process according to claim 1 for the preparation of 3-phenoxybenzyl-[3-(2,2-dichlorovinyl)-2,2-dimethyl-cyclopropanecarboxylate], which comprises reacting 3-(2,2-dichlorovinyl)-2,2-dimethyl-cyclopropanecarboxylic acid with dimethylchloromethylydene-ammonium chloride and further reacting dimethyl-[3-(2,2-dichlorovinyl)-2,2-dimethylcyclopropanecarbonyloxy]-methylydene-ammonium chloride obtained with 3-phenoxybenzyl alcohol in the presence of said organic base.

10. A process according to claim 1 for the preparation of benzyl-[3-(2,2-dichlorovinyl)-2,2-dimethyl-cyclopropanecarboxylate] which comprises reacting 3-(2,2-dichlorovinyl)-2,2-dimethyl-cyclopropanecarboxylic acid with dimethyl-chloromethylydene-ammonium chloride and further reacting of dimethyl-[3-(2,2-dichlorovinyl)-2,2-dimethyl-cyclopropanecarbonyloxy]-methylydene-ammonium chloride with benzyl alcohol in the presence of said organic base.

11. A process according to claim 1 for the preparation of 3-phenoxybenzyl-(+)-trans-chrysanthemate which comprises reacting (+)-trans-chrysanthemic acid with dimethyl-chloromethylydene-ammonium chloride and further reacting dimethyl-(+)-trans-chrysanthemoyloxy-methylydene-ammonium chloride obtained with 3-phenoxy-benzylalcohol in the presence of an organic solvent.

12. A process according to claim 1 for the preparation of 1β-hydroxy-2β-(cis-but-2-enyl)-3-methylydene-cyclopentane-4β-yl-(+)-trans-chrysanthemate which comprises reacting (+)-trans-chrysanthemic acid with dimethyl-chloromethylydene-ammonium chloride and further reacting dimethyl-(+)-trans-chrysanthemoyloxy-methylydene-ammonium chloride obtained with 4β-hydroxy-3-methylydene-2β-(cis-but-2-enyl)-1β-cyclopentanol in the presence of an organic base.

* * * * *